United States Patent
Martin

(10) Patent No.: US 10,306,932 B1
(45) Date of Patent: Jun. 4, 2019

(54) UNDERWEAR WITH INTEGRATED LUMBAR SUPPORT PAD

(71) Applicant: Jose Martin, Miami, FL (US)

(72) Inventor: Jose Martin, Miami, FL (US)

( * ) Notice: Subject to any disclaimer, the term of this patent is extended or adjusted under 35 U.S.C. 154(b) by 208 days.

(21) Appl. No.: 15/437,725

(22) Filed: Feb. 21, 2017

(51) Int. Cl.
| A41B 9/12 | (2006.01) |
| A41B 9/00 | (2006.01) |
| A41B 9/14 | (2006.01) |
| A41F 9/02 | (2006.01) |
| A61F 5/02 | (2006.01) |

(52) U.S. Cl.
CPC ............. *A41B 9/12* (2013.01); *A41B 9/001* (2013.01); *A41B 9/14* (2013.01); *A41F 9/025* (2013.01); *A61F 5/028* (2013.01)

(58) Field of Classification Search
CPC .. A41B 9/12; A41B 9/001; A41B 9/14; A61F 5/028; A61F 9/025
See application file for complete search history.

(56) References Cited

U.S. PATENT DOCUMENTS

| 2,118,797 A | 5/1938 | Sanders |
| 2,684,486 A | 7/1954 | Purves |
| 3,207,155 A | 9/1965 | Cullen |
| 4,702,239 A | 10/1987 | Ichikawa |
| 6,053,883 A * | 4/2000 | Schiek, Sr. ............. A61F 5/028 602/19 |
| 6,099,490 A * | 8/2000 | Turtzo .................... A61F 5/028 2/311 |
| D698,118 S | 1/2014 | Denning |
| 2004/0083537 A1 | 5/2004 | Mosha |
| 2014/0018763 A1 * | 1/2014 | Evenson ........... A61F 13/49006 604/385.14 |
| 2014/0026295 A1 | 1/2014 | McIntyre |

FOREIGN PATENT DOCUMENTS

EP 0196667 A1 10/1986

\* cited by examiner

*Primary Examiner* — Khaled Annis

(57) ABSTRACT

The underwear with integrated lumbar support pad is an orthopedic device. The underwear with integrated lumbar support pad is an article of loin wear. The underwear with integrated lumbar support pad is adapted for use with a person. The article of loin wear has incorporated into it a back brace that provides lumbar support to the person wearing the underwear with integrated lumbar support pad. The underwear with integrated lumbar support pad adds a belt fastener within the waistband region generally associated with loin wear. Moreover, the belt fastener includes a lumbar support apparatus to accomplish the function of the underwear with integrated lumbar support pad. The underwear with integrated lumbar support pad comprises an article of loin wear and a brace.

9 Claims, 6 Drawing Sheets

UNDERWEAR WITH INTEGRATED LUMBAR SUPPORT PAD

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science, more specifically, an orthopedic lumbar support incorporated into an undergarment.

SUMMARY OF INVENTION

The underwear with integrated lumbar support pad is an orthopedic device. The underwear with integrated lumbar support pad is an article of loin wear. The underwear with integrated lumbar support pad is adapted for use with a person. The article of loin wear has incorporated into it a back brace that provides lumbar support to the person wearing the underwear with integrated lumbar support pad. The underwear with integrated lumbar support pad adds a belt fastener within the waistband region generally associated with loin wear. Moreover, the belt fastener includes a lumbar support apparatus to accomplish the function of the underwear with integrated lumbar support pad. The underwear with integrated lumbar support pad comprises an article of loin wear and a brace.

These together with additional objects, features and advantages of the underwear with integrated lumbar support pad will be readily apparent to those of ordinary skill in the art upon reading the following detailed description of the presently preferred, but nonetheless illustrative, embodiments when taken in conjunction with the accompanying drawings.

In this respect, before explaining the current embodiments of the underwear with integrated lumbar support pad in detail, it is to be understood that the underwear with integrated lumbar support pad is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the underwear with integrated lumbar support pad.

It is therefore important that the claims be regarded as including such equivalent construction insofar as they do not depart from the spirit and scope of the underwear with integrated lumbar support pad. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
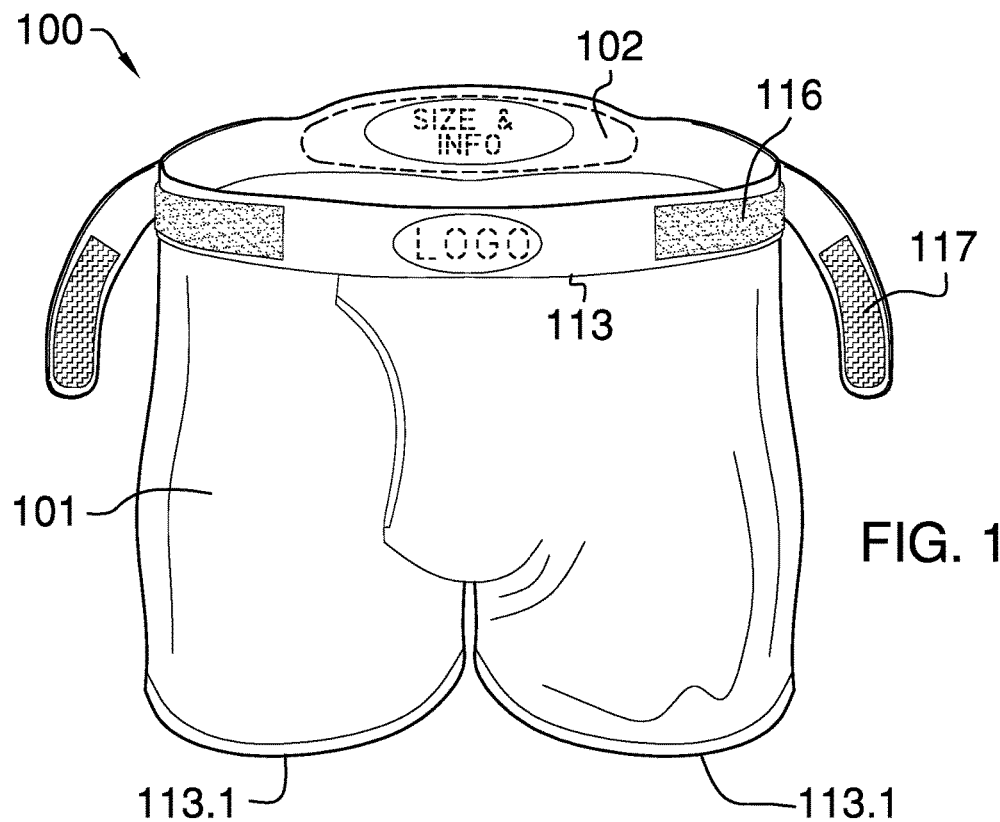
FIG. 1 is a perspective view of an embodiment of the disclosure.
Figure 2:
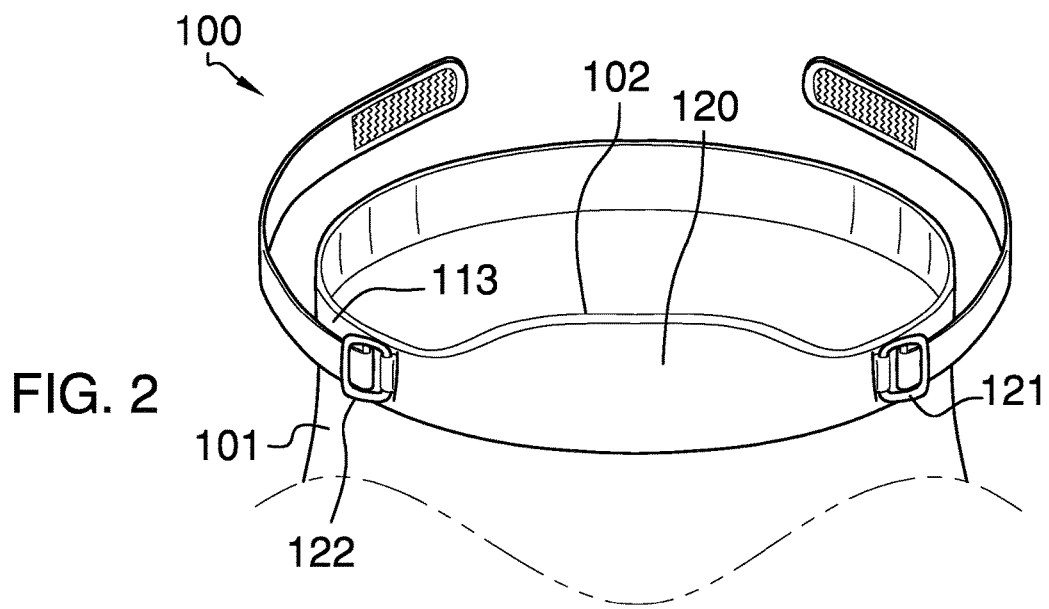
FIG. 2 is a rear view of an embodiment of the disclosure.
Figure 3:
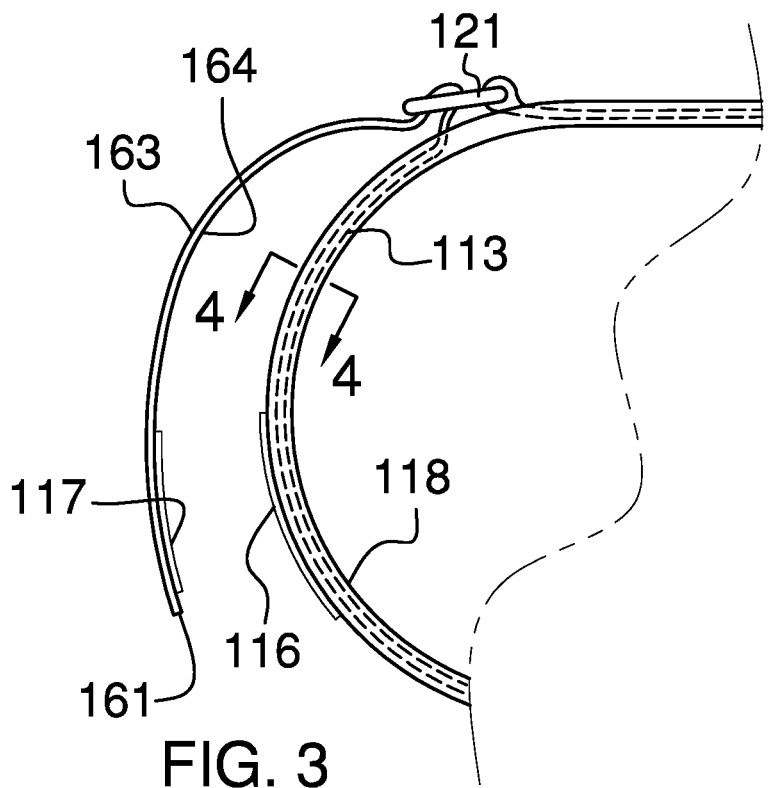
FIG. 3 is a detail view of an embodiment of the disclosure.
Figure 4:
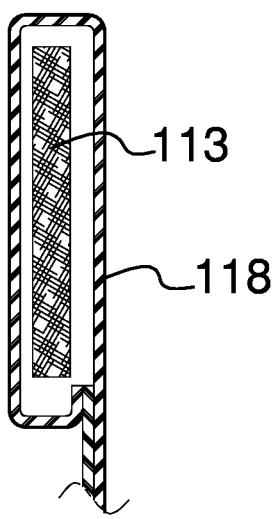
FIG. 4 is a detail view of an embodiment of the disclosure.
Figure 5:
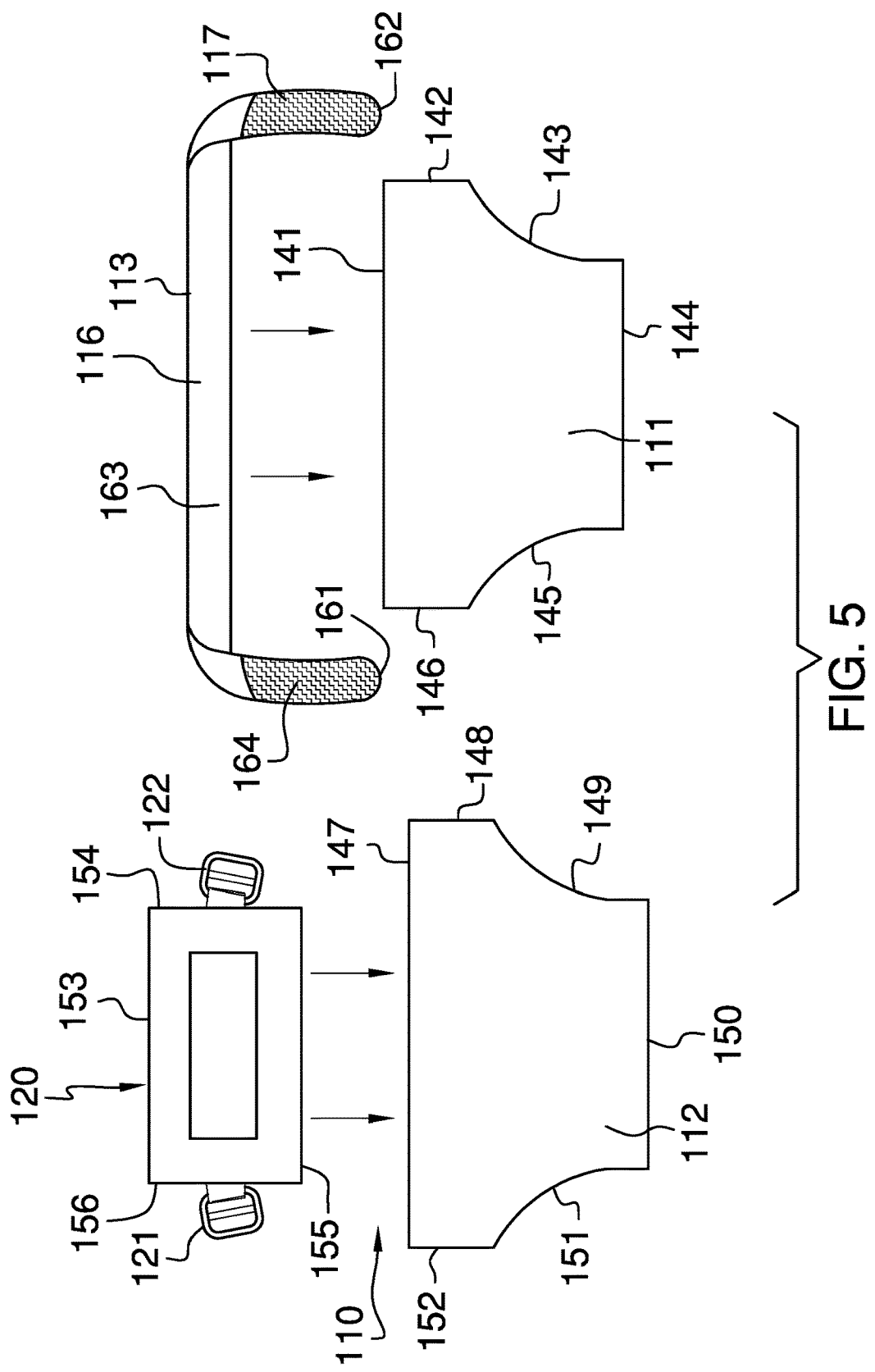
FIG. 5 is a detail view of an embodiment of the disclosure.
Figure 6:
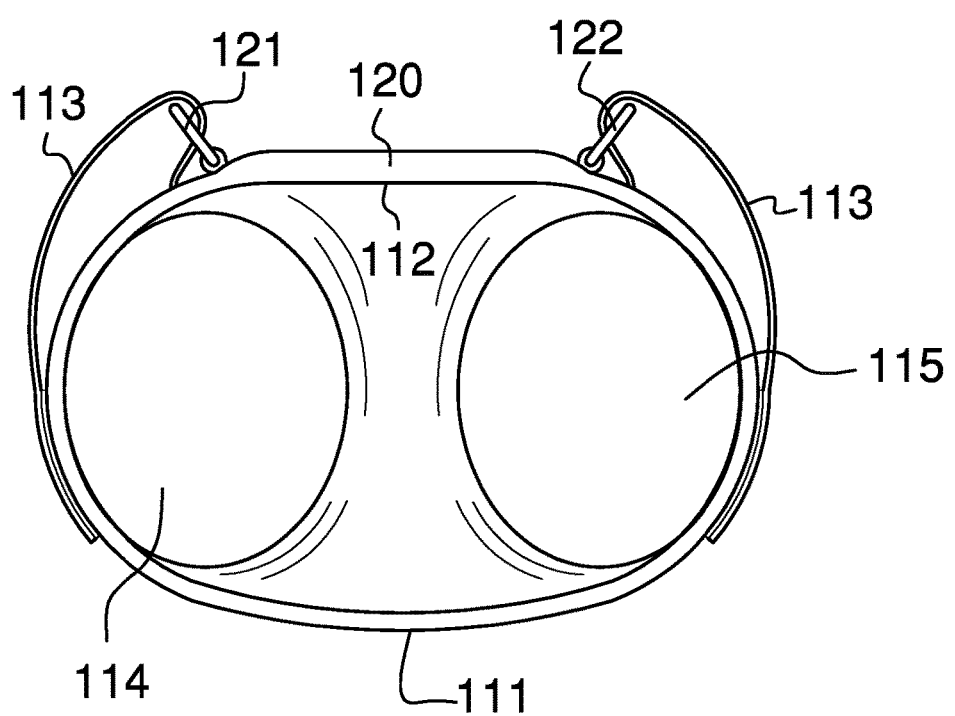
FIG. 6 is a top view of an embodiment of the disclosure.
Figure 7:
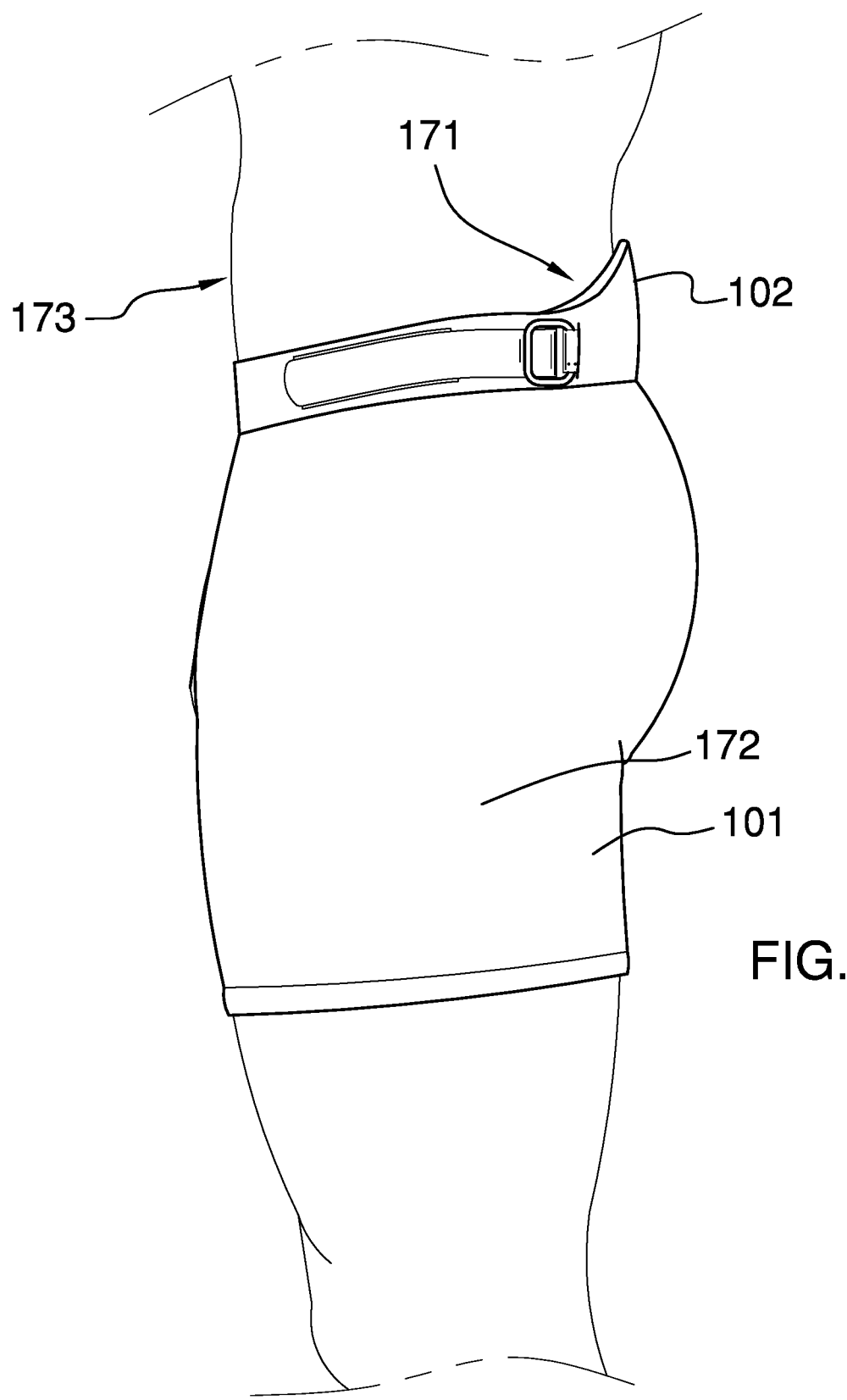
FIG. 7 is an in use view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 8.

The underwear with integrated lumbar support pad 100 (hereinafter invention) is an orthopedic device. The invention is an article of loin wear 101. The invention 100 is adapted for use with a person 173. The article of loin wear 101 has incorporated into it a back brace 102 that provides lumbar support to the person 173 (hereinafter wearer) wearing the invention 100. The invention 100 places a belt strap inside of the elastic portion of the waistband generally associated with loin wear 101 with a lumbar support apparatus to accomplish the function of the invention 100. The invention 100 comprises an article of loin wear 101 and a brace 102.

The article of loin wear 101 is an undergarment that is worn over the loin region 172. The use and manufacture of an article of loin wear 101 is well known and documented in the textile and apparel arts. The article of loin wear 101 comprises a plurality of panels 110 and an belt fastener 113. The article of loin wear 101 is further defined with a first leg hole 114 and a second leg hole 115. The first leg hole 114 is a hole formed within the article of loin wear 101 such that the leg of the wearer 173 will fit through the first leg hole 114. The second leg hole 115 is a hole formed within the article of loin wear 101 such that the leg of the wearer 173 will fit through the second leg hole 115. The loin wear 101 is further defined with a bottom edge 113.1 for each leg associated therewith.

The plurality of panels 110 are a plurality of individual components that are joined together to form the article of loin wear 101. The plurality of panels 110 comprises a first panel 111 and a second panel 112.

The first panel 111 is a first cut textile that is used to form the article of loin wear 101. As shown most clearly in FIG. 5, the first panel 111 is further defined with a first edge 141, a second edge 142, a third edge 143, a fourth edge 144, a fifth edge 145, and a sixth edge 146. The first edge 141 is a straight edge that forms the top of the article of loin wear 101. The second edge 142 is a straight edge that forms the side of the article of loin wear 101. The third edge 143 is a curved edge that forms the second leg hole 115 of the article of loin wear 101. The fourth edge 144 is a straight edge that forms the bottom of the article of loin wear 101. The fifth edge 145 is a curved edge that forms the first leg hole 114 of the article of loin wear 101. The sixth edge 146 is a straight edge that forms the side of the article of loin wear 101.

The second panel 112 is a second cut textile that is used to form the article of loin wear 101. As shown most clearly in FIG. 5, the second panel 112 is further defined with a seventh edge 147, an eighth edge 148, a ninth edge 149, a tenth edge 150, an eleventh edge 151, and a twelfth edge 152. The seventh edge 147 is a straight edge that forms the top of the article of loin wear 101. The eighth edge 148 is a straight edge that forms the side of the article of loin wear 101. The ninth edge 149 is a curved edge that forms the second leg hole 115 of the article of loin wear 101. The tenth edge 150 is a straight edge that forms the bottom of the article of loin wear 101. The eleventh edge 151 is a curved edge that forms the first leg hole of the article of loin wear 101. The twelfth edge 152 is a straight edge that forms the side of the article of loin wear 101.

The belt fastener 113 is a non-elastic webbing that is used to: 1) secure the article of loin wear 101 to the wearer 173 during the use of the invention 100, and 2) secure the brace 102 against the lumbar region 171 of the wearer 173.

The belt fastener 113 is further defined with a first end 161, a second end 162, a first surface 163, and a second surface 164. The first end 161 is a first terminating end of the webbing that forms the belt fastener 113. The first end 161 of the belt fastener 113 is inserted through the first loop 121 of the brace 102. The second end 162 is a second terminating end of the webbing that forms the belt fastener 113. The second end 162 of the belt fastener 113 is inserted through the second loop of the brace 102.

The belt fastener 113 is further defined with a first hook or loop surface 116 and a second hook or loop surface 117. In the first potential embodiment of the disclosure, the belt fastener 113 is formed such that the first surface 163 of the belt fastener 113 forms the first hook or loop surface 116 presented by the belt fastener 113. The belt fastener 113 is formed such that the second surface 164 of the belt fastener 113 forms the second hook or loop surface 117 presented by the belt fastener 113. The first hook or loop surface 116 and the second hook or loop surface 117 are integrally formed as part of the non-elastic webbing that forms the belt fastener 113 and are not subsequently added. Such webbings are readily and commercially available.

The belt fastener 113 inserts through a channel 118 to form the waistband of the invention 100. The channel 118 is a textile that is attached to the one or more panels selected from the plurality of panels 110. The channel 118 is a sleeve structure made of an elastic waist band material that is folded over, and through which the belt fastener 113 is inserted such that the belt fastener 113 is attached to the invention 100.

The brace 102 is an orthopedic device that is used to support the lumbar region 171 of the back of the wearer 173. The brace 102 comprises a support panel 120, a first loop 121, and a second loop 122.

The support panel 120 is a textile structure that is placed (under tension) in contact with the lumbar region 171 of the wearer 173. The support panel 120 is used to redistribute the forces applied to the lumbar region 171 of the wearer 173 to a larger surface area thereby reducing the direct pressure on the lumbar region 171. The support panel 120 is further defined with a thirteenth edge 153, a fourteenth edge 154, a fifteenth edge 155, and a sixteenth edge 156. The thirteenth edge 153 is a straight edge. The fourteenth edge 154 is a straight edge. The fifteenth edge 155 is a straight edge. The sixteenth edge 156 is a straight edge.

The first loop 121 is a readily and commercially available first D ring that is attached to the sixteenth edge 156 of the support panel 120 such that the first end 161 of the belt fastener 113 can be inserted through the first loop 121 in a manner that secures the support panel 120 to the lumbar region 171 of the wearer 173. The second loop 122 is a readily and commercially available second D ring that is attached to the fourteenth edge 154 of the support panel 120 such that the second end 162 of the belt fastener 113 can be inserted through the second loop 122 in a manner that secures the support panel 120 to the lumbar region 171 of the wearer 173.

The plurality of seams 130 are a collection of seams that are used to connect the components of the invention 100 during the assembly of the invention 100. The plurality of seams 130 comprises a first seam 131, a second seam 132, a third seam 133, a fourth seam 134, a fifth seam 135. The first seam 131 is a sewn seam. The second seam 132 is a sewn seam. The third seam 133 is a sewn seam. The fourth seam 134 is a sewn seam. The fifth seam 135 is a sewn seam.

Figure 8:
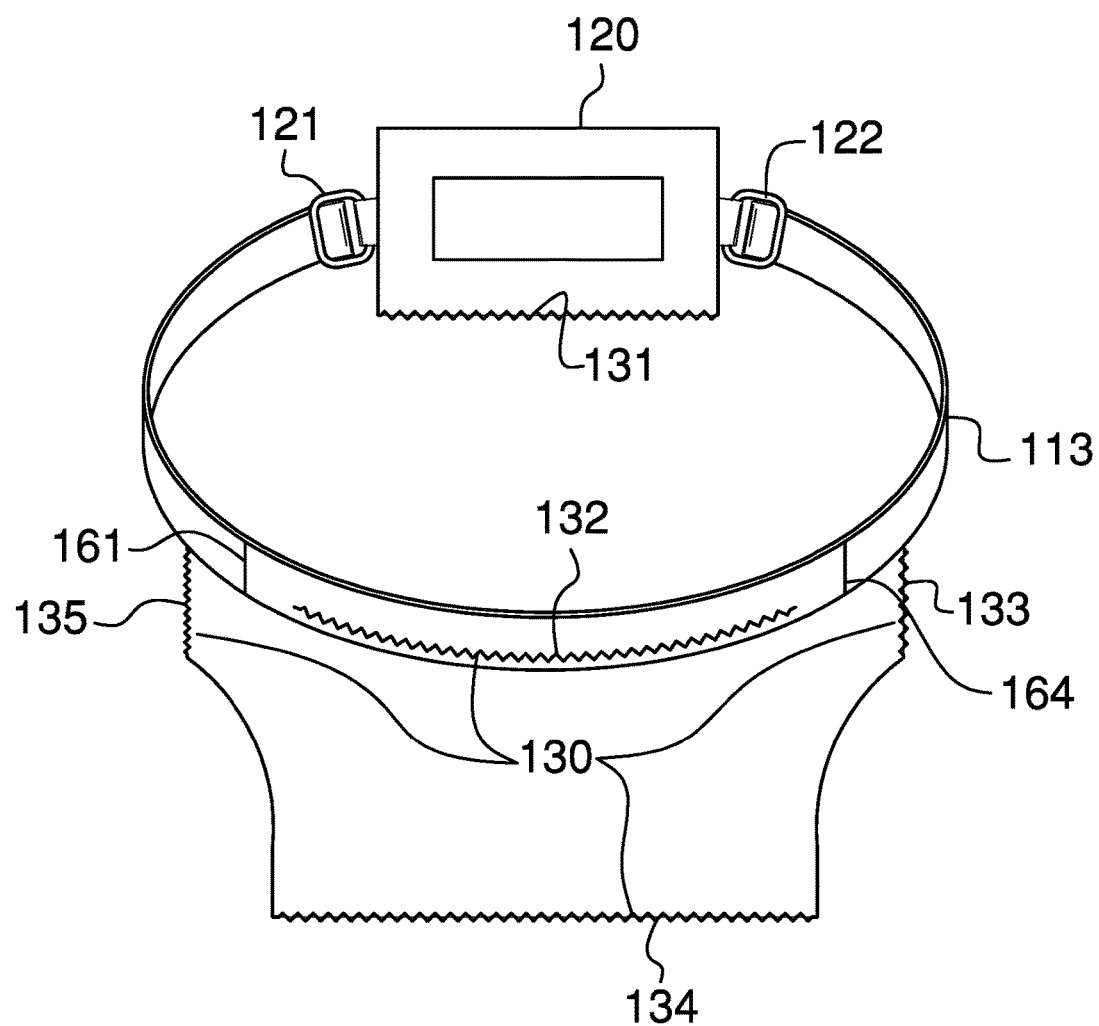
FIG. 8 is a detail view of an embodiment of the disclosure.

As shown most clearly in FIG. 8, the first seam 131 attaches the fifteenth edge 155 of the support panel 120 to the seventh edge 147 of the second panel 112. The second seam 132 attaches the center of the belt fastener 113 to the first edge 141 of the first panel 111. The third seam 133 attaches the second edge 142 of the first panel 111 to the eighth edge 148 of the second panel 112. The fourth seam 134 attaches the fourth edge 144 of the first panel 111 to the tenth edge 150 of the second panel 112. The fifth seam 135 attaches the sixth edge 146 of the first panel 111 to the twelfth edge 152 of the second panel 112.

To use the invention 100, the article of loin wear 101 is put on as normal. The first end 161 is inserted through the first loop 121. The second end 162 is inserted through the second loop 122. The first end 161 is secured to the belt fastener 113 by pressing the second hook or loop surface 117 of the first end 161 against the first hook or loop surface 116 of the body of the belt fastener 113. The second end 162 is secured to the belt fastener 113 by pressing the second hook or loop surface 117 of the second end 162 against the first hook or loop surface 116 of the body of the belt fastener 113.

The following definitions were used in this disclosure:

Band: As used in this disclosure, a band is a flat loop of material.

Fastener: As used in this disclosure, a fastener is a device that is used to join or affix two objects. Fasteners generally comprise a first element, which is attached to the first object and a second element which is attached to the second object such that the first element and the second element join to affix the first object and the second object. Common fasteners include, but are not limited to, zippers, snaps, buttons, buckles, quick release buckles, or hook and loop fasteners.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook or loop surface" with the understanding that when the two objects are fastened together one of the two objects will have a hook surface and the remaining object will have the loop surface.

Loin: As used in this disclosure, the loin refers to a region of the human body that comprises the pelvis, the buttocks, and the adjacent sexual organs.

Loin Wear: As used in this disclosure, loin wear refers to underclothing that is intended to be worn over the loin region with the occasional exception of the buttocks. Commonly used synonyms for loin wear include, but are not limited to, bikini bottoms, boxer briefs, boxers, briefs, calzones, drawers, French cut, g string, knickers, loincloth, panties, panty, shorts, skivvies, thong, trunks, underpants, undies, and unmentionables.

Loop: As used in this disclosure, a loop is the length of a first linear structure including, but not limited to, lines, cords, or ribbons, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Lumbar: As used in this disclosure, the lumbar refers to the lower back region of a person. Depending on the context, the lumbar region is either: 1) adjacent to the loin region of a person; or, 2) incorporates the upper portion of the loin region of a person.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Textile: As used in this disclosure, a textile is a material that is woven, knitted, braided or felted. Synonyms in common usage for this definition include fabric and cloth.

Undergarment: As used in this disclosure, undergarment refers to garments that are intended to be worn next to the skin. An undergarment is often worn in conjunction with an outer layer of clothing.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An orthopedic support apparatus comprising:
   an article of loin wear and a brace;
   wherein the brace is attached to the article of loin wear;
   wherein the article of loin wear is an undergarment that is adapted to be worn over a loin region;
   the orthopedic support apparatus is an orthopedic device;
   wherein the orthopedic support apparatus is adapted for use with a wearer;
   wherein the orthopedic support apparatus is adapted to provide lumbar support to the wearer;
   wherein the article of loin wear comprises a plurality of panels and a belt fastener;
   wherein the belt fastener attaches to the plurality of panels;
   wherein the article of loin wear is further defined with a first leg hole and a second leg hole;
   wherein the plurality of panels comprises a first panel and a second panel;
   wherein the first panel is a first cut textile;
   wherein the second panel is a second cut textile that is used to form the article of loin wear;
   wherein the first panel is further defined with a first edge, a second edge, a third edge, a fourth edge, a fifth edge, and a sixth edge;
   wherein the second panel is further defined with a seventh edge, an eighth edge, a ninth edge, a tenth edge, an eleventh edge, and a twelfth edge;
   wherein the first edge is a straight edge that forms the top of the article of loin wear;
   wherein the second edge is a straight edge that forms the side of the article of loin wear;
   wherein the third edge is a curved edge that forms the second leg hole of the article of loin wear;

wherein the fourth edge is a straight edge that forms the bottom of the article of loin wear;
wherein the fifth edge is a curved edge that forms the first leg hole of the article of loin wear;
wherein the sixth edge is a straight edge that forms the side of the article of loin wear;
wherein the seventh edge is a straight edge that forms the top of the article of loin wear;
wherein the eighth edge is a straight edge that forms the side of the article of loin wear;
wherein the ninth edge is a curved edge that forms the second leg hole of the article of loin wear;
wherein the tenth edge is a straight edge that forms the bottom of the article of loin wear;
wherein the eleventh edge is a curved edge that forms the first leg hole of the article of loin wear;
wherein the twelfth edge is a straight edge that forms the side of the article of loin wear;
wherein the belt fastener is a webbing
wherein the belt fastener is adapted to secure the article of loin wear to the wearer;
wherein the belt fastener is adapted to secure the brace against the lumbar region of the wearer;
wherein the belt fastener is further defined with a first end, a second end, a first surface, and a second surface;
wherein the belt fastener is further defined with a first hook or loop surface and a second hook or loop surface;
wherein the belt fastener is formed such that the first surface of the belt fastener forms the first hook or loop surface presented by the belt fastener;
wherein the belt fastener is formed such that the second surface of the belt fastener forms the second hook or loop surface presented by the belt fastener;
wherein the first hook or loop surface and the second hook or loop surface are integrally formed as part of the webbing;
wherein the belt fastener is disposed within a channel in one or more panels selected from the plurality of panels;
wherein the brace comprises a support panel, a first loop, and a second loop;
wherein the first loop attaches to the support panel;
wherein the second loop attaches to the support panel;
wherein the first end of the belt fastener is inserted through the first loop of the brace and the second end is a second terminating end of the webbing that forms the belt fastener;
wherein the support panel is a textile structure that is in contact with the lumbar region of the wearer;
wherein the support panel redistributes the forces applied to the lumbar region of the wearer to a larger surface area thereby reducing the direct pressure on the lumbar region;
wherein the support panel is further defined with a thirteenth edge, a fourteenth edge, a fifteenth edge, and a sixteenth edge;
wherein the thirteenth edge is a straight edge;
wherein the fourteenth edge is a straight edge;
wherein the fifteenth edge is a straight edge;
wherein the sixteenth edge is a straight edge.

2. The orthopedic support apparatus according to claim 1 wherein the first loop is a first D ring;
wherein the second loop is a second D ring.

3. The orthopedic support apparatus according to claim 2 wherein the first loop attaches to the sixteenth edge of the support panel;
wherein the second loop attaches to the fourteenth edge of the support panel;
wherein the fourteenth edge is distal from the sixteenth edge.

4. The orthopedic support apparatus according to claim 3 wherein a plurality of seams are a collection of seams that are used to connect a components of the orthopedic support apparatus during the assembly of the orthopedic support apparatus;
wherein the plurality of seams comprises a first seam, a second seam, a third seam, a fourth seam, a fifth seam;
wherein the first seam is a sewn seam;
wherein the second seam is a sewn seam;
wherein the third seam is a sewn seam;
wherein the fourth seam is a sewn seam;
wherein the fifth seam is a sewn seam.

5. The orthopedic support apparatus according to claim 4 wherein the first seam attaches the fifteenth edge of the support panel to the seventh edge of the second panel.

6. The orthopedic support apparatus according to claim 5 wherein the second seam attaches the belt fastener to the first edge of the first panel.

7. The orthopedic support apparatus according to claim 6 wherein the third seam attaches the second edge of the first panel to the eighth edge of the second panel;
wherein the fourth seam attaches the fourth edge of the first panel to the tenth edge of the second panel;
wherein the fifth seam attaches the sixth edge of the first panel to the twelfth edge of the second panel.

8. The orthopedic support apparatus according to claim 7 wherein the first end is inserted through the first loop;
wherein the second end is inserted through the second loop.

9. The orthopedic support apparatus according to claim 8 wherein the first end is secured to the belt fastener by pressing the second hook or loop surface of the first end against the first hook or loop surface of the body of the belt fastener;
wherein the second end is secured to the belt fastener by pressing the second hook or loop surface of the second end against the first hook or loop surface of the body of the belt fastener.

* * * * *